US009968209B2

(12) United States Patent
Maranon

(10) Patent No.: US 9,968,209 B2
(45) Date of Patent: May 15, 2018

(54) AROMATIC IDENTIFICATION FOR A FOOD CONTAINER

(75) Inventor: Patrick Maranon, Floirac (FR)

(73) Assignees: Julien-Maxime Maranon, Bordeaux (FR); Dominique Gomez, Floirac (FR)

( * ) Notice: Subject to any disclaimer, the term of this patent is extended or adjusted under 35 U.S.C. 154(b) by 1528 days.

(21) Appl. No.: 13/364,541

(22) Filed: Feb. 2, 2012

(65) Prior Publication Data

US 2013/0199266 A1 Aug. 8, 2013

(51) Int. Cl.

| | |
|---|---|
| ***G01N 33/02*** | (2006.01) |
| ***A47F 7/28*** | (2006.01) |
| ***G09F 23/06*** | (2006.01) |
| ***G09F 5/00*** | (2006.01) |
| ***B65D 23/14*** | (2006.01) |

(52) U.S. Cl.
CPC .............. *A47F 7/286* (2013.01); *B65D 23/14* (2013.01); *G09F 5/00* (2013.01); *G09F 23/06* (2013.01); *B65D 2203/12* (2013.01)

(58) Field of Classification Search
CPC ........... G01N 33/02; A47F 7/286; A47F 7/30; B65D 23/14; B65D 23/12; B65D 2203/12; G09F 23/06; G09F 5/00; G09F 2005/046
USPC .................... 73/23.34, 31.05; 239/34; 222/3; 220/200; 215/227, 235, 258
See application file for complete search history.

(56) References Cited

U.S. PATENT DOCUMENTS

| | | | | |
|---|---|---|---|---|
| 3,149,431 | A * | 9/1964 | Blish | 40/311 |
| 4,161,284 | A * | 7/1979 | Rattan | 239/43 |
| 4,258,004 | A * | 3/1981 | Valenzona et al. | 422/123 |
| 5,635,229 | A * | 6/1997 | Ray | A23L 1/22008 206/205 |
| 5,932,147 | A * | 8/1999 | Chen | 261/30 |
| 6,102,224 | A * | 8/2000 | Sun et al. | 215/252 |
| 8,740,110 | B2 * | 6/2014 | Gruenbacher et al. | 239/34 |
| 2005/0178185 | A1 * | 8/2005 | Negri | 73/23.34 |
| 2010/0104715 | A1 * | 4/2010 | Norris et al. | 426/394 |
| 2010/0143203 | A1 * | 6/2010 | Miro Amenos et al. | 422/116 |
| 2011/0278370 | A1 * | 11/2011 | Glydon | B65D 5/38 239/6 |
| 2012/0006909 | A1 * | 1/2012 | Zhang et al. | 239/34 |
| 2013/0043245 | A1 * | 2/2013 | Griffis | 220/200 |

FOREIGN PATENT DOCUMENTS

| | | | |
|---|---|---|---|
| DE | 19837356 | * | 2/2000 |
| FR | 2689669 | A1 | 10/1993 |
| WO | WO 2009/156114 | * | 12/2009 |

* cited by examiner

*Primary Examiner* — Paul West
*Assistant Examiner* — Xin Zhong
(74) *Attorney, Agent, or Firm* — Bechman & LaPointe, P.C.

(57) ABSTRACT

Olfactory identification of the contents of a bottle, in particular wine, or any food container, intended to facilitate the choice of the product by a novice consumer making a purchase is enabled. A support, such as an enclosure attached to a bottle and, inside, a substance aromatized with the aromas representative of the contents of the bottle, make it possible to assist with the selection.

9 Claims, 4 Drawing Sheets

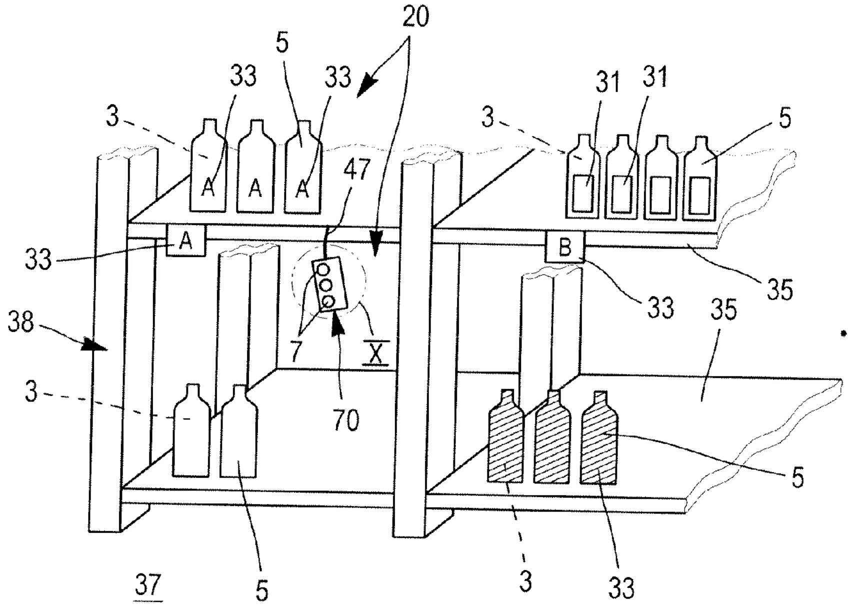
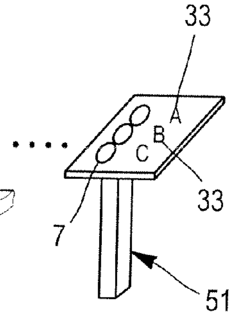
FIG. 11
FIG. 8
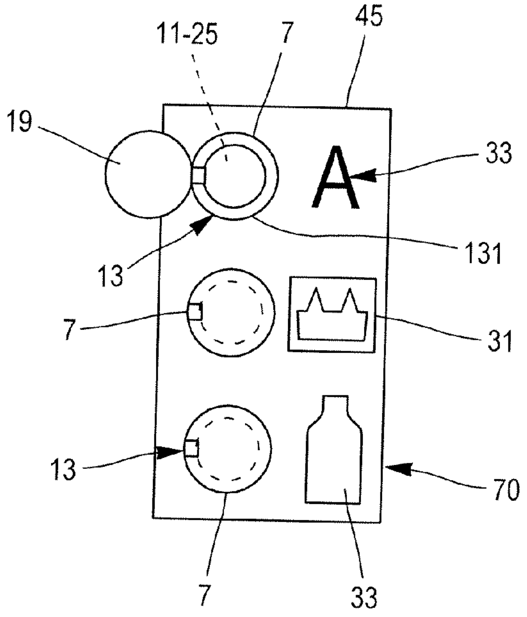
FIG. 10

AROMATIC IDENTIFICATION FOR A FOOD CONTAINER

BACKGROUND

This invention is intended in general to enable the olfactory identification of a food product placed in a container, by means of its main aroma(s) reproduced in an external support.

It thus relates, in general, to the field of distribution of wine or other food products in closed containers.

A food product container has a label presenting the product.

For example, a bottle of wine is generally in glass and is specifically intended to contain wine.

The shape of the bottle provides information on the origin of the wine that it contains.

This has been the case for a long time: the shape of the bottle and its color remain the only distinctive features, for those who understand their meaning, with the label providing information on the contents and origin of the wine. It is known to sometimes affix or paste, in addition to the label, a medallion to provide additional or promotional information. However, this is only to be read or visually experienced.

For example, patent U.S. Pat. No. 3,149,431 discloses a card with a ring in the upper portion enabling it to be placed around the neck.

The patent FR 2 689 669 proposes a label with a portion pierced with a hole through which the neck passes, and, by extension, a lower portion glued to the body of the bottle.

In the presence of an unknown appellation of a bottle of wine or other beverage that is discovered on a shelf or display at a store, it is almost impossible to know whether the contents corresponds to one's taste: Chardonnay, Merlot, etc. for wines, bourbon and whiskey, for beverages produced by distillation, mocha, Arabica, etc. for coffees, and so on. It is therefore difficult to know what works the best for a given customer, in a defined product category.

SUMMARY OF THE INVENTION

Under these conditions, the following is proposed:

A first objective is to associate the container of a food product with an information support, for reasons of practicality, certainty and relevance for the consumer, while ensuring safety of use and preservation of the aroma over time.

To satisfy the first objective, a device is proposed for olfactory identification of a food product placed in a container, which device includes a support containing an aroma representative of an odor characteristic of said food product, in which the support includes a box that can be opened and closed by a covering, and which contains a solid substrate having said aroma.

It is recommended that the box be rigid, that the covering be rigid and attached to the receptacle of the box by a hinge, a screw or a clip, and that the substrate be non-removable from the container.

The box/container connection may be a detachable connection or a removable attachment, or, in a common form, integrated.

It is recommended that the support be non-impervious and contain a solid substrate containing said at least one aroma.

This "non-imperviousness" means that there will not be a seal; however, when the support is closed, the odor that it contains will not be notably diffused.

It is also recommended that the support include a box, preferably rigid:

closed by a covering that can be opened, and that contains said at least one representative aroma, which is not placed in an impervious enclosure.

In both cases, the safety of use and preservation will be promoted.

A second objective is to ensure a practical and lasting association between a food product and at least one aroma.

To satisfy this second objective, an assembly is proposed that therefore enables olfactory identification of the food product, which assembly includes:

a closed vessel containing said food product and that can be opened in order to access the product, a support including an aroma representative of an odor characteristic of the food product contained in the vessel, in which the support includes a container that can be opened and closed and that contains a substrate aromatized with said aroma, and a connection is established between the support and the closed vessel, thus enabling olfactory pre-identification of the food product contained in the vessel.

It is recommended that the support be securely connected to the vessel and contain a solid substrate having said aroma.

It is also recommended that the support include a receptacle that contains the substrate and a covering movably connected to the receptacle, capable of being opened and closed numerous times.

A third objective is to facilitate an informed choice of beverages at a retail location or a beverage consumption location.

To satisfy this third objective, a display stand is proposed, which includes:

a plurality of first supports each containing an aromatic substance representative of a characteristic odor of at least one of said beverages, and which can be closed and opened in order to be smelled, a second support to be held:

holding said first supports, having references to said beverages, in which a connection is established between each aromatic substance and the beverage reference corresponding to it, thus enabling, by olfactory pre-identification, said at least one beverage to be selected from a more numerous selection.

It is recommended that the display stand be such that:

the first supports include boxes each containing a different aromatic substance, the second support to be in the form of a booklet, in which the first supports are held, and each connection to be either a text or an image relating to the beverage considered and placed in correspondence with the associated first support.

Thus, the consultation of the display stand will be practical and user-friendly, and the display stand will be capable of being handled.

A fourth objective is to facilitate the choice of a food product and access to it, at a retail location, such as a supermarket, in which the products are each arranged in a closed container offered for sale.

The display stand proposed for this purpose is such that it includes:

at least one first support containing an aromatic substance representative of a characteristic odor of at least one of said food products, and which can be opened and closed, for olfactory identification of said product, at least one second support having a plurality of food products in their respective containers, including that which the aromatic substance represents, in which the first supports and at least one among the second support and the containers are arranged at a distance from one another, and a connection established between the aromatic substance and the closed container containing the food product that it represents, thus enabling said container to be found at the retail location, in reference to its olfactory identification.

The aforementioned arrangement at a distance means that at least:

either the first supports are not held by the containers from which they are placed at a distance (in FIGS. 8 and 9, below, it can be seen that the supports 7 are at a distance from the closed vessels 5; they are not, however, necessarily at a distance from the shelf (second support) on which these vessels are placed), or the first supports are at a distance from the second supports (shelves/displays 35 below): they are, for example, arranged on a distant rack or on a distinct display, attached to one of said second supports, or held by the containers themselves, and therefore not placed directly on the second supports.

It is recommended that the connection be defined by securing the first supports to the second support, with a visual correspondence of proximity between the groups of containers and the first supports corresponding to them.

In addition, it is recommended in both cases that the second support be a standing structure placed on the ground.

Another solution is a display stand including:

a plurality of first supports:

individually attached to each container, containing an aromatic substance representative of an odor characteristic of said food product, and that can be closed and opened in order to be smelled, a second support in which said food products are placed in their respective containers individually equipped with the first aromatic support characterizing them.

A fifth objective is to propose a relevant solution making it possible to prepare the conditions to initiate a person to test one of a number of beverages, and to perform this initiation.

The method proposed for this purpose is such that:

a selection is made of at least one of said beverages, of which at least one of the characteristic aromas is identified, the person smells an odor representative of said at least one identified aroma, the person tests the beverage selected, and, by means of the reference to the odor smelled, the person is encouraged to find said at least one characteristic aroma in the beverage tested.

It is recommended that, prior to the test, said odor be incorporated in a solid substrate.

A sixth objective is to propose a relevant solution making it possible to provide assistance in the selection by a person of at least one of a number of beverages of the same category, belonging to the following categories: fruit juice, vegetable juice, sodas, flavored waters, beverages produced by infusion, alcoholic beverages produced by fermentation (wines, in particular), beverages produced by distillation, and beverages produced from a grist.

A first type of method proposed for this purpose is such that:

one of said categories is considered, at least one of the characteristic aromas of each of said beverages capable of being chosen, in the category considered, is identified, for each of said beverages, an aromatic substance is developed of which the odor is representative of said at least one identified aroma, each of said beverages is individually contained in a closed container, each container is equipped with a closed support containing said aromatic substance, which support can be opened and closed, when making the choice, said person smells the odor of each substance representative of at least some of the beverages among those capable of being chosen, in the category considered.

A second type of method proposed in order to provide assistance in the selection is such that:

one of said categories is considered, at least one of the characteristic aromas of each of said beverages capable of being chosen, in the category considered, is identified, for each of said beverages, an aromatic substance is developed of which the odor is representative of said at least one identified aroma, said aromatic substances developed are combined on a support that is secured to a display stand, and a connection is established between each aromatic substance and a closed container containing the beverage that it represents, thus enabling this container to be found in the store, and when making the choice, said person smells the odor of each substance representative of at least some of the beverages among those capable of being chosen, in the category considered, then, in reference to the odors smelled, chooses those that he or she wants, for which he or she finds the containers by means of the connections.

It is also recommended that the connection include a visual identification, constituted by said container or a label provided on the container.

Preferably, for ease and safety of handling, it is recommended that the support include a rigid element that will have been secured to the display stand and that will rigidly hold a box:

that will contain the aromatic substance in the form of a solid substrate, and that will be opened in order to release the odor, and that can be closed back up with a rigid covering.

In one aspect, it is therefore proposed that olfactory identification of a wine contained in a bottle be enabled by means of its main aromas, reproduced in a small external container that can be opened, and which container is applied to the bottle in the form of a pendant around the neck.

In particular, the choice of a beverage, including a wine, a coffee, a tea or a white or a brown spirit, will be facilitated by adding an olfactory aspect to the uniquely visual criteria that have long been known.

In particular, for a wine, it is possible to use the aromas characteristic of the grape varieties used, or, in a more thorough manner, the aromas specific to the contents of a bottle of wine from a precise location or winegrowing area.

BRIEF DESCRIPTION OF THE DRAWINGS

Below is a discussion of preferred embodiments, with reference to illustrative figures, which, like the embodiments, are non-limiting, in which.

DETAILED DESCRIPTION OF THE PREFERRED EMBODIMENT(S)

Figure 1:
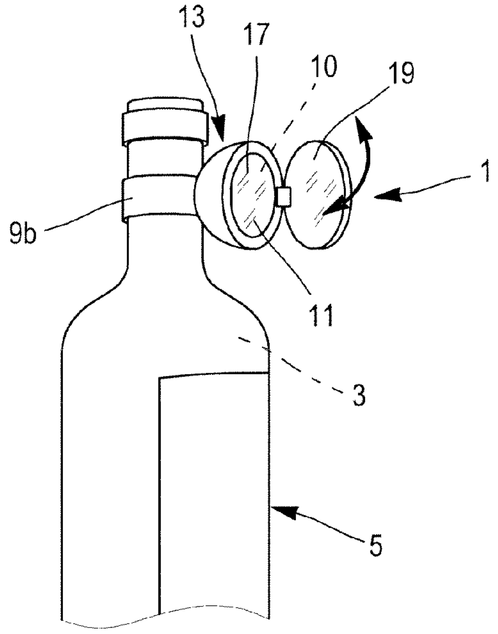
FIGS. 1 and 2 diagrammatically show a vessel with a support (or device) for olfactory identification, FIG. 3 diagrammatically shows the support according to FIG. 1, FIG. 4 diagrammatically shows an alternative of said support, FIG. 5 diagrammatically shows an approach to the choice of a beverage and the arrangement on store shelves, FIGS. 6 and 7 diagrammatically show, open and closed, a restaurant wine menu equipped with the envisaged olfactory identification device, FIGS. 8 and 9 diagrammatically show to display stands equipped with the envisaged olfactory identification device, FIGS. 10 and 11 diagrammatically show two aromatic substance supports capable of being used in particular in a store, with FIG. 10 showing an enlargement of detail X of FIG. 8.
Figure 2:
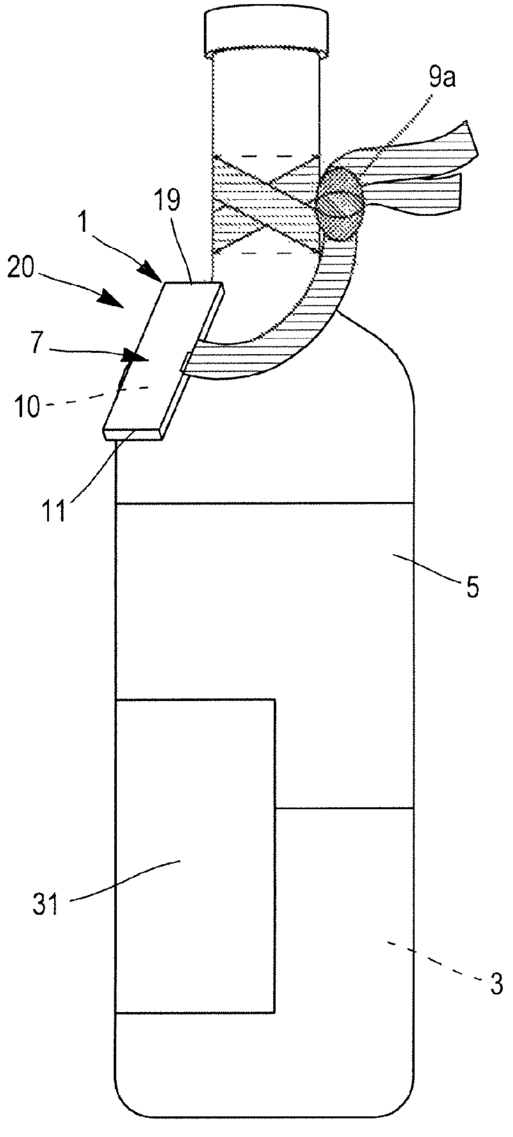

FIGS. 1 and 2, in particular, show a device 1 for olfactory identification of a food product 3 placed in a container 5 that is, in principle, non-impervious. It is preferably a vessel.

The device 1 includes a support 7 containing at least one aroma (designated as 10) representative of a characteristic odor of the food product 3.

The device 1 also includes a detachable structural connection 9*a* (FIG. 2) and a removable attachment 9*b* (FIGS. 1 and 3), for thus connecting the support 7 to the container 5.

Figure 3:
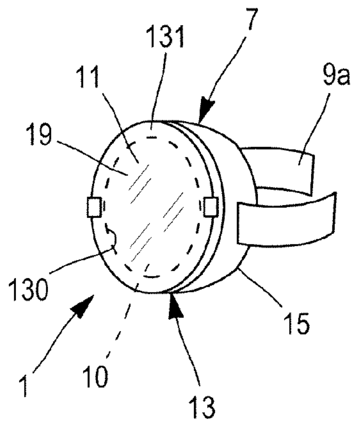

In FIGS. 1 and 3, the removable attachment 9*b* includes two rigid but slightly resiliently deformable lugs, for forming a clamp suitable for clamping a bottle, and in this case its neck.

The aroma 10 will be volatile, or at least capable of being diffused, or smelled by a human nose, in the vicinity of the (open) support 7. It is not placed in an enclosure, which is impervious before being cut or pierced, as in FR 2 558 697.

The detachable connection 9*a* (FIG. 2) can be a resistant strip or wire placed around the neck of a bottle, which can define the container 5.

The detachable connection 9*a* can alternatively be a resistant strip or wire embedded around a box, preferably rigid, containing another food product 3, such as pâté or caviar.

The removable attachment 9*b* can be a resilient split ring to be resiliently force-fit (such as a clip) around the container: box, bottle, jar, etc. It can also be a non-resilient ring.

It is recommended that the connection 7/container 5 be secure.

It is preferable for the support 7 to contain a solid substrate 11 having an aroma. To combine practicality of use and durability, the support 7 will be securely connected to the container 5 and will contain said aromatized substrate.

The aroma will preferably be an aromatic extract or an essential oil or a combination of such oils, or a water-based aromatic composition.

Preferably, the support 7 will contain the substrate 11, in a non-refillable manner.

For ease of use and durability, it is recommended (FIG. 3) that the substrate 11 and the aroma be defined respectively, in a mixture, by:

- either a solid polymer or a wax (one example of a material could be malleable under heat and have a melting temperature of between 70° C. and 95° C.), and
- a volatile compound developed from an oil base, a water base, a powder base or an alcohol base.

In a preferred alternative (FIG. 4), because it is durable and easy to handle, the substrate and said aroma may respectively include:

- a solid porous material 25 (such as a porous stone), and
- a volatile compound developed from an oil base, an alcohol base or a water base, with which said solid porous material is impregnated.

In another alternative, grains and seeds, soil, sand, gravel, foams, fabrics, textile elements, inorganic materials and organic matter can be cited.

It is recommended that the support 7 include a rigid box, which is closed 13, and which can be opened (in order to smell) and which contains said at least one representative aroma 10.

In the case of a solid porous material, it is recommended that it have, with the box, a non-removable connection, which is either:

- a rigid attachment (glue),
- or a fastening with complementary shapes, inside the box 13 and outside the material, respectively, or a substrate 11, which is solid, and thus permanently fixed inside the box.

This second solution is preferable in the case of wax or a solid polymer.

The support 7 can include one or more aromas representative of the typical odor of the food product contained in the vessel, according to the more or less basic or complex odor to be smelled.

If, as preferred, a solid substrate 11 is used, it will preferably include at least one of the following: an essentially plant-based material, an essentially inorganic material and an essentially organic material.

To hold the substrate 11 in place, it is recommended that it be in the form of a solid block placed in close contact with an inner face 130 of a wall of the box 13, which thus will permanently hold it. FIG. 3 shows the peripheral edge that surrounds the opening of the vessel 15 and holds the substance 11 (in this case a wax or a polymer that can be poured when heated) behind it, after it has been poured into the vessel.

It is recommended that, if a box 13 is used, it include:

- a vessel 15 that contains the support 7 and has an opening 17 through which said at least one aroma 10 is diffused, and
- a mobile covering 19, which is non-removable from the vessel and which can be opened and closed from above the opening 17.

It is recommended that the covering be pivotably connected (by a hinge) to the receptacle 15, or even clipped or screwed on (in an un-screwable manner), but preferably held on the receptacle by a connection.

A transparent or translucent covering is preferable.

Thus, even if it is dispersed, in the solid substrate, the aroma 11 (water- or oil-based in principle) is in direct permanent contact with the air; only the covering 19 limits this contact when it is closed (although in a non-impervious manner).

In a practical solution, the box 13 will include a receptacle 15 and a covering 19 arranged on the receptacle. This covering will directly open and close (without an intermediate sealed enclosure) an opening 17 of the receptacle through which said at least one aroma will be diffused when the covering is open.

FIGS. 1 and 2 also show the embodiment of an assembly 20 therefore enabling the desired olfactory identification, or pre-identification, of the food product considered.

This assembly includes:

a closed vessel 5 containing said food product 3 and which can be opened in order to recover said product, and a support 7 including the aroma(s) 10 representative of the characteristic odor of the food product contained in the vessel.

Figure 4:
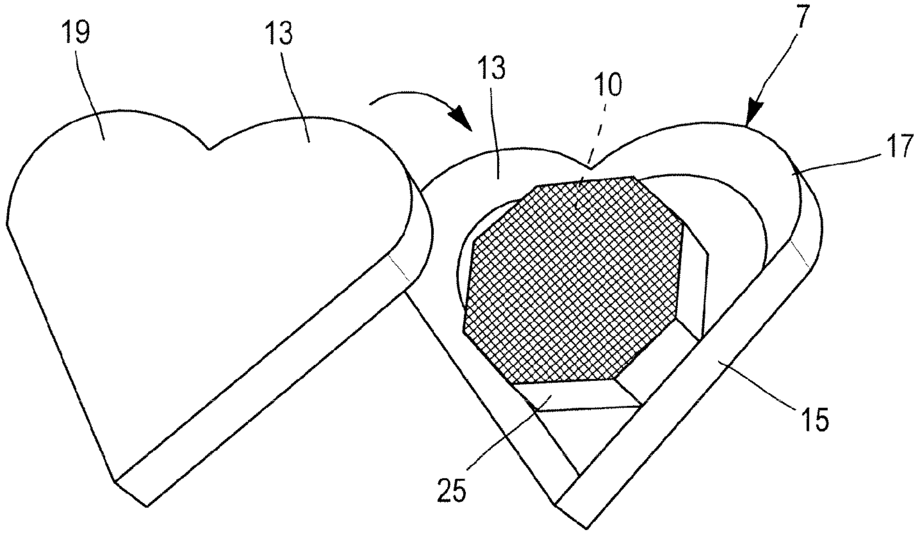

In FIG. 4, the support 7 includes a closed box 13 that can be opened and closed, and that contains the substance 11. This substrate is a block aromatized with the aroma(s).

Again, it is recommended that this substrate 11 be non-enclosed in a protective film before being pierced or cut in order to release the aroma(s).

It is also recommended that this assembly 20, like the device 1, be:

free of aromatized microcapsules, and/or free of an impervious flexible enclosure, and/or free of printed structures having a dedicated aroma.

They are thus differentiated from the disclosures of WO 2009 156114 or FR 2 558 697.

The above must make it possible to implement the following.

In this regard, the invention relates first to the method for initiating and preparing the conditions for initiating a person to a testing of one among a number of beverages.

Preferably by using all or some of the means described above, the following steps will be capable of being carried out:

a) first, at least one of the beverages to be tested will be selected. Preferably before the next step, at least one of the 10 characteristic aromas of this beverage will have been identified. For this, a chemical laboratory analysis will have been conducted, or an enologist will have been called upon.

For a wine, it is possible to cite apple, apricot, banana, black pepper, violet, musk, oak and tobacco aromas. For a whisky, it is possible to cite woody (vanilla, sherry, roasted), grain, floral (heath, fresh flower, grass, foliage) or peat aromas.

b) then, the person to be initiated will smell an odor representative of said at least one identified aroma. This odor will be that of the aroma 10 released from the support 7.

c) the person will then test the beverage selected, even if the order of b) and c) can optionally be reversed.

d) and, by reference to the odor smelled, the person will be encouraged to find said at least one characteristic aroma in the beverage tested.

It is also recommended that:

prior to the selection of the beverage, not just one but a plurality of characteristic aromas of said beverage will preferably be identified, prior to the test, said representative odor is created from a plurality of basic odors individually representative of at least one of said aromas identified.

Thus, the subtlety of the analysis will be reinforced.

That said, to maintain a fast, user-friendly, simple approach, it is recommended that, again, prior to the test, said odor be incorporated (for example by dispersion) in a non-enclosed or non-encapsulated solid substrate.

In addition, to expand the selection offered, it is recommended, during the selection, that a plurality of different beverages contained in each different container or vessel 5 be selected, each of which will have been provided with a support 7, each aromatized with said odor, which will be different from one support to another.

In the following two cases, it will be suggested how to provide assistance in the selection by a person of at least one among a number of beverages in the same category, belonging to the following categories: fruit juice, vegetable juice, sodas, flavored waters, beverages produced by infusion, alcoholic beverages produced by fermentation, beverages produced by distillation, and beverages produced from a grist.

Figure 5:
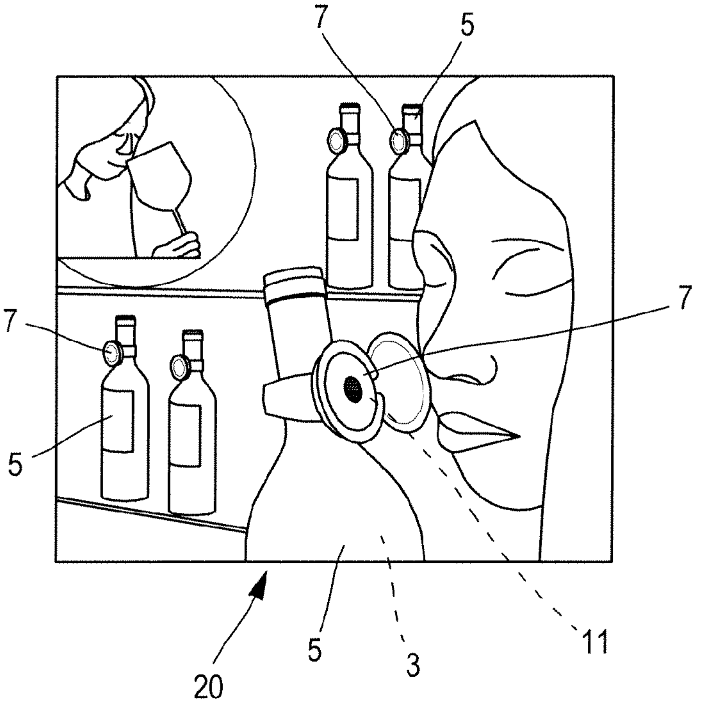

For this, it is recommended, according to a first approach, that the following be performed:

first, one of the aforementioned categories is considered, then, at least one of the aromas 10 characteristic of each of the beverages can be chosen, in the category considered, for each of the aforementioned beverages, an aromatic substance, which can be the substrate 11, 25, of which the odor is representative of said at least one aroma identified, is developed each of said beverages is individually contained in a closed container/vessel 5, each container is equipped with a closed support 7 containing said aromatic substance, which can be opened and closed again (as in FIGS. 1, 2 and 5), then, as in FIG. 5:

when making the choice, the person concerned smells the odor of each substance representative of at least some of the beverages among those capable of being chosen, in the category considered (as shown in FIG. 5, it is possible to envisage smelling the beverage itself).

a group of these beverages is then preferably selected, for example from the shelves.

In addition, it is recommended that, by reference to the odor smelled, the person is encouraged to choose the beverages that he or she wishes to acquire.

According to a second alternative approach, it is possible to carry out the following, as explained below and diagrammatically shown in FIGS. 6, 7, 8 and 9:

first, again, one of the aforementioned categories will be considered; then, at least one of the aromas characteristic of said beverages can be chosen, in the category considered, for each of said beverages, an aromatic substance will be developed, of which the odor is representative of said at least one aroma identified; this substance can, in particular, be substrate 11 or 25, said aromatic substances developed will be combined on a support 7 that is secured to a display stand, such as 29, 38 or 40 (FIGS. 6, 8 and 9) and a connection 33 will be established between each aromatic substance and a closed container or vessel 5 containing the beverage that it represents, thus making it possible to find said container in the store, and when making the choice, the person will smell the odor of each substance (such as 11, 25) representative of at least some of the beverages among those capable of being chosen, in the category considered, then, in reference to the odors smelled, will choose those desired, of which the containers 5 are found by means of the connections (the bottles at the bottom left-hand side of FIG. 8 are thus excluded from the choice).

In this case, it is recommended that the connection 33 include a visual identification 30 of either said container/vessel 5 and/or a label 31 with which the container may be equipped by being affixed thereto. It may be a paper label glued to a bottle. The connection and the label (or said container/vessel 5) will include common information (message, color, illustration, etc.) enabling one to refer to the other.

Figure 9:
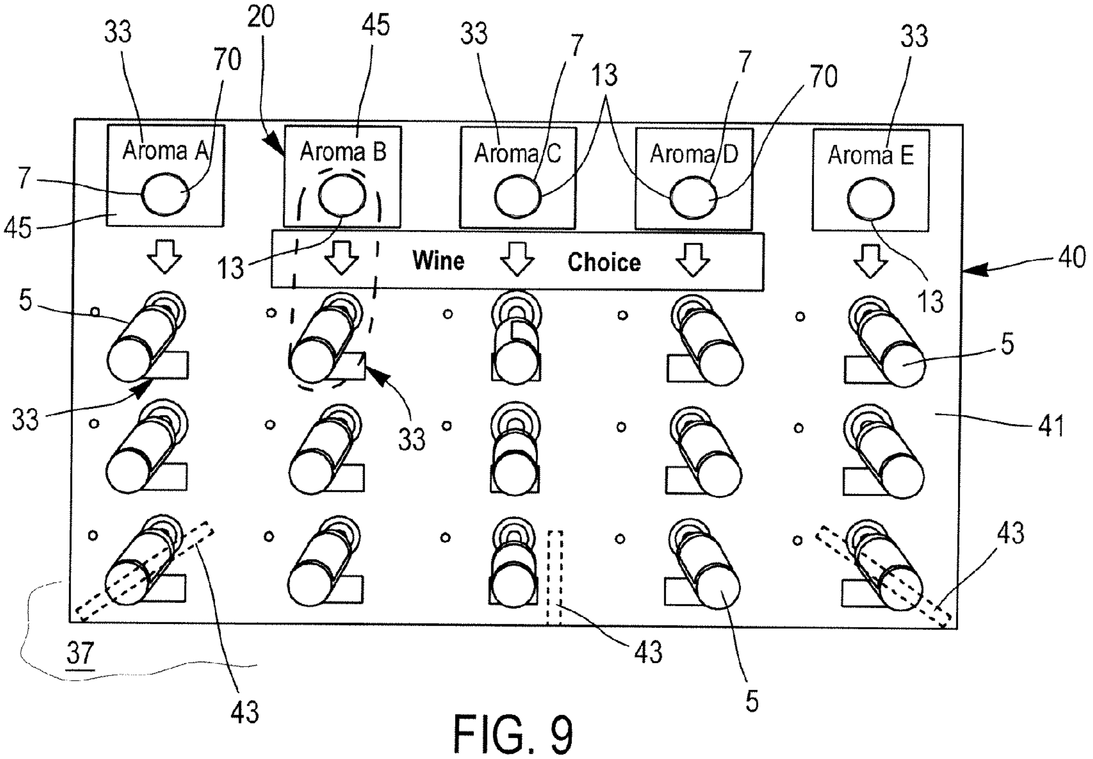

In FIGS. 9 and 9, the support 7 includes a rigid element, such as a plate or a mini-poster 70, which will have been secured to the display stand 29, and which will rigidly hold a box (such as 13):

- which will contain the aromatic substance in the form of a solid substrate (11, 25),
- and which will be opened so as to release the odor and which can be closed back up with a rigid covering, such as 19.

Figure 6:
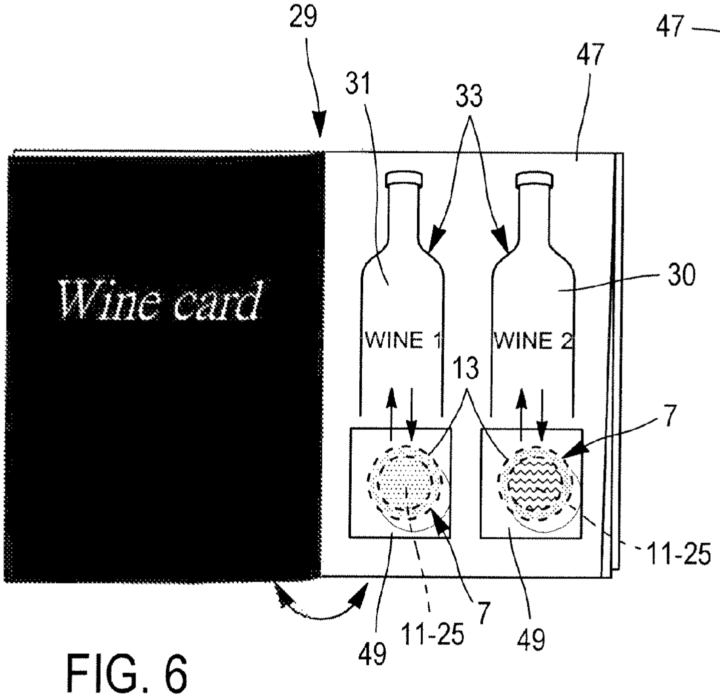
Figure 7:
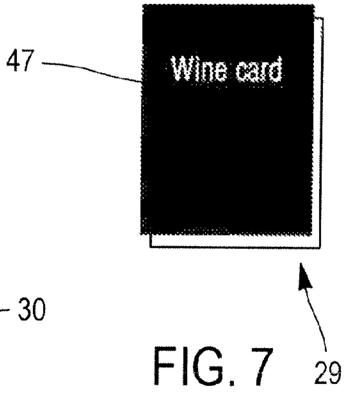

Now, concerning the way in which to offer the food products concerned for sale, each packaged in their closed containers, two methods are preferred, as shown in FIGS. 6 and 7, solution B, and 8-11, solution A (with the specification that the support 70, FIGS. 8 and 9, may however be replaced by the booklet of FIGS. 6 and 7).

Solution A:

In this case, two versions are presented:

First, as shown in FIG. 8, it is possible to have a display stand 38 including:

- for the olfactory identification of the product considered, a (group of) first openable supports 7, individually containing the aromatic substance 11, 25 already described, therefore representative of an odor characteristic of at least one of the food products offered for sale, at the appropriate location, such as a supermarket,
- to offer said products for sale, a second support, such as a store shelving system 35, therefore having a plurality of food products in their respective containers (vessels 5 if they are drinks), including that which the aromatic substance represents, in which the first supports 7 and either the second support (shelves 35) or the containers (vessels 5) are arranged at a distance from one another, and
- a connection 33 established between the aromatic substance, such as 11, 25, and the closed container or vessel 5 containing the food product that said substance represents. This will make it possible to find said container at the retail location 37, in reference to its olfactory identification.

Then, as in FIG. 9, it is possible to provide another display stand 40, including:

- a plurality of first supports 7 each containing an aromatic substance 11, 25 representative of a characteristic odor of a plurality of food products to be sold, in which each support can be closed and opened in order to be smelled,
- a second support, such as a panel 41 erected and stabilized by lugs 43, having the food products in their respective containers (such as 5), which are distributed by groups (in this case by columns, under the respective boxes 13), according to the aromatic substances representing them,
- and, again, a connection 33 established, on the display stand (in this case at the top of each column) between one of said aromatic substances determined and the group of containers corresponding thereto, which again enables, by olfactory pre-identification, one such group to be selected at the retail location from a more numerous set.

Concerning the connection 33, it is recommended in both cases that it be defined by securing the first supports 7 to the second support 35, 41 with a visual correspondence of proximity between the groups of containers and the first supports corresponding thereto.

In FIGS. 8 and 9, this attachment is performed by tightly holding the boxes 13 (then without means 9*a* and 9*b*) in an opening provided through a plate such as 70 attached directly to the second support (FIG. 9, mini-poster) or by a connection such as a flexible cable 47.

The solution of FIG. 5, which involves attaching each first support 7 to the vessel/container, in this case the bottle 55 and placing the vessels on shelves, also has its benefits: it enables an aroma to be associated directly with the vessel holding the box 13 containing it. There is no more searching the shelves of the store, as can be understood by looking at FIG. 5.

Solution B:

Again, optionally in a store, but preferably in a restaurant, the display stand 29 of FIGS. 5 and 6 is envisaged, including:

- again, a plurality of first supports 7, 13 each containing the aromatic substance already presented,
- a second support to be held 47:
  - having said first supports,
  - having references to said beverages, for identification thereof (grape variety, appellation, winegrower, etc.),
  - and in which a connection, such as 33, is established between each aromatic substance and the beverage reference corresponding thereto, again enabling the preferred beverage to be selected by olfactory pre-identification, from a more numerous group.

In this last case, it is recommended that:

- the first supports include boxes, such as 13, each containing a different aromatic substance 11, 25,
- the second support 47 be in the form of a booklet in which the first supports are held, and
- each connection 33 is either a text or an image relating to the beverage considered and placed in correspondence with the associated first support. As shown, this may be the image of the bottle itself and/or its label 31, for example.

FIG. 7 shows the closed booklet 47; in FIG. 6, it is opened to one of its pages.

In particular, the first supports, such as these boxes 13, may be slipped into a transparent open pouch, produced on the top of an internal page of a rigid booklet defining, for example, in a restaurant, a cardboard or plasticized wine menu. An attachment in an opening provided through a page or sheet, in particular cardboard or plasticized, is also possible.

FIG. 11 shows a rack 51 holding the (first) supports 7, and, in visual correspondence, the connections 33 for identification of the containers/vessels concerned. This rack can in particular replace the support 70, at the end of an aisle, for example, of the wine or alcohol shelf in a store. The mini-poster "B" of FIG. 8 is a reference thereto.

From the above, it should be understood that, in each case, an olfactory identification device will be found, such as that designated 1, therefore intended to enable the aromas contained to be accessible to the nose of the future consumer.

The invention claimed is:

1. An assembly enabling olfactory identification of a food product, which assembly includes:

- a closed vessel containing said food product and that can be opened in order to access the product,
- a support including an aroma representative of an odor characteristic of the food product contained in the vessel,
- in which the support includes a container that can be opened and closed and that contains a solid substrate aromatized with said aroma, in which the support is securely connected to the closed vessel, thus enabling olfactory pre-identification of the food product contained in the vessel.

2. The assembly according to claim 1, wherein the support includes a box closed by a covering that can be opened and closed and that contains a non-enclosed block having said aroma.

3. The assembly according to claim 1, wherein the assembly is free of at least one of the following: aromatized microcapsules, and a printed structure having a dedicated aroma.

4. The assembly according to claim 1, wherein the solid substrate is free of a protective film.

5. The assembly according to claim 2, wherein the covering is translucent.

6. The assembly according to claim 2, wherein the covering is transparent.

7. The assembly according to claim 1, wherein the support and said aroma are defined, respectively, in a mixture, by one of a solid polymer and a wax, and a volatile compound developed from one of an oil base, a water base, and a powder base and an alcohol base.

8. The assembly according to claim 7, wherein the solid polymer has a melting temperature of between 70 degrees Centigrade and 95 degrees Centigrade.

9. The assembly according to claim 7, wherein the wax has a melting temperature of between 70 degrees Centigrade and 95 degrees Centigrade.

* * * * *